US005181848A

United States Patent [19]
Griffith

[11] Patent Number: 5,181,848
[45] Date of Patent: Jan. 26, 1993

[54] DENTAL MIRROR

[76] Inventor: Walter L. Griffith, 51 Cavalier Rd. East, Scottsville, N.Y. 14546

[21] Appl. No.: 805,972

[22] Filed: Dec. 12, 1991

[51] Int. Cl.⁵ ............................................. A61B 1/24
[52] U.S. Cl. ...................................................... 433/30
[58] Field of Search ........................ 433/30, 31; 128/22

[56] References Cited

U.S. PATENT DOCUMENTS

| | | | |
|---|---|---|---|
| 1,387,770 | 8/1921 | Dolbey | 433/31 X |
| 1,764,455 | 6/1930 | Kulik | 433/31 |
| 3,613,246 | 10/1971 | Zdarsky | 433/30 |
| 4,408,991 | 10/1983 | Engel | 433/30 |
| 5,052,925 | 10/1991 | Stalcup | 455/30 |

FOREIGN PATENT DOCUMENTS

| | | | |
|---|---|---|---|
| 3546379 | 7/1987 | Fed. Rep. of Germany | 433/30 |
| 306722 | 2/1929 | United Kingdom | 433/31 |

Primary Examiner—Gene Mancene
Assistant Examiner—Nicholas D. Lucchesi
Attorney, Agent, or Firm—Robert J. Bird

[57] ABSTRACT

A dental mirror includes a handle with an enclosure head on the end. The enclosure has a cover which is partially mirrored and partially transparent, a light source within it, and a concave reflector around the light source to reflect light through the transparent portion of the cover, the reflected light converging in front of the mirror. Heat from the light source keeps the mirror free of fogging.

9 Claims, 1 Drawing Sheet

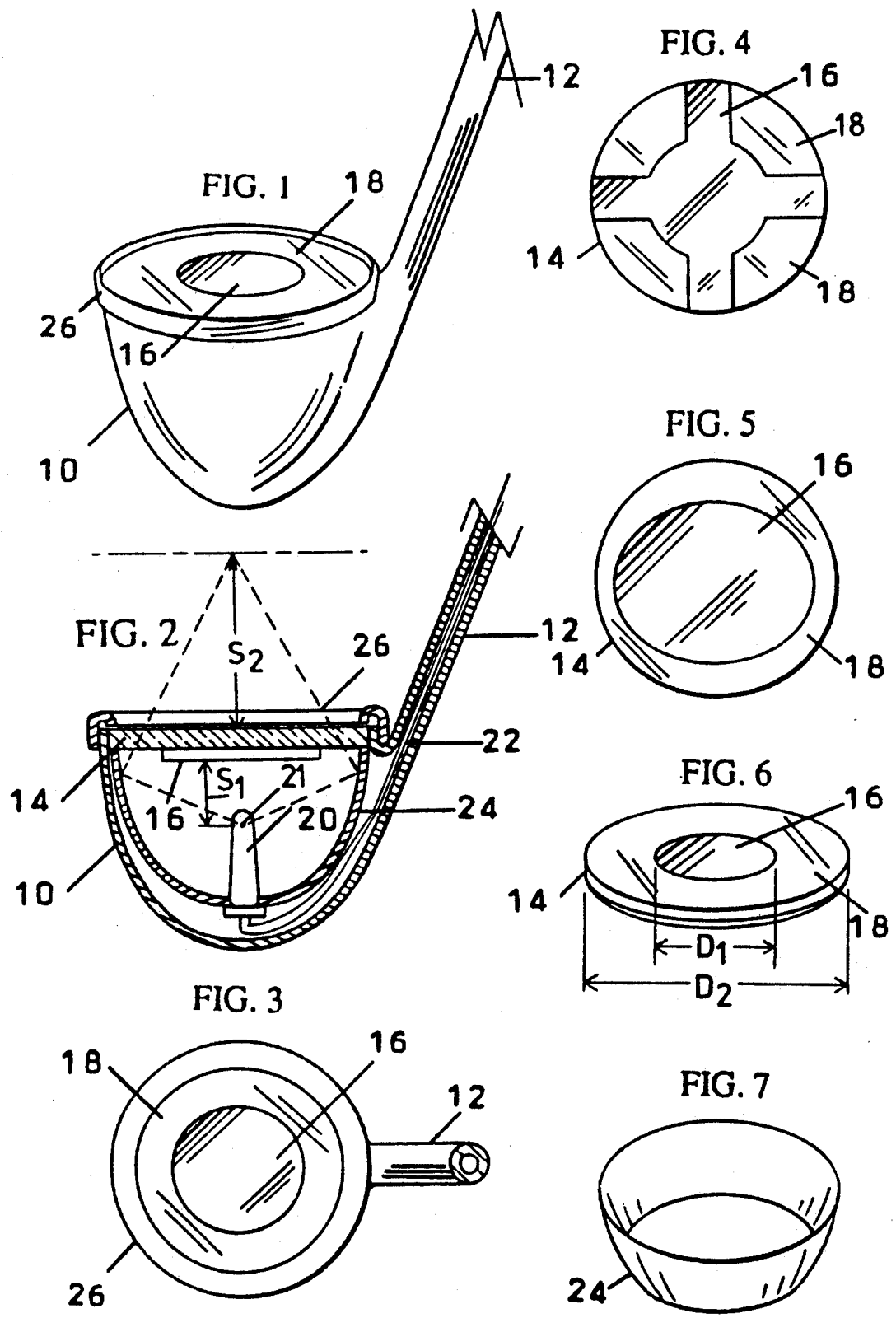

DENTAL MIRROR

This invention is a dental mirror providing object space illumination.

BACKGROUND INFORMATION

In modern times, fluoride in public water supplies and in toothpaste has been very effective to reduce dental caries. A consequence of this is that people now make fewer visits to the dentist than was common a generation ago. It therefore becomes important for individuals to pay closer attention to the condition of their own teeth and gums. A dental mirror is necessary to enable one to view the back surfaces of ones own teeth and gums.

Ordinary dental mirrors which have long been used to view the back surfaces of teeth and gums include simply a small mirror mounted at an angle at the end of a handle. These do not provide illumination within the mouth, and they get fogged up with the breath of the subject.

There have been attempts in the prior art to solve both the illumination and fogging problems of dental mirrors. U.S. Pat. No. 3,158,935 issued to Rosenthal in 1964 attempted to provide lighting with neon tubing, and to defog the mirror with a wiper mechanism attached to it.

U.S. Pat. No. 1,764,455 issued to Kulik in 1930 is the most relevant prior art that I know of. Kulik discloses a dental mirror including a handle with an enclosure on the end. A mirror on top of the enclosure has a hole through its center. A light bulb is behind the mirror, and some of its light passes through the center hole of the mirror to provide illumination in front of the mirror. Illumination provided by the Kulik device interferes with the user's view of the mirror image because the illumination is said to be intense and it is right in the center of the mirror (and the mirror image, which it is desired to see clearly). Furthermore, the light produced by the Kulik device does not converge in front of the mirror to provide concentrated illumination. Instead, the light necessarily diverges in front of the mirror and does not provide concentrated illumination.

It is an object of this invention to provide a dental mirror with concentrated and unobtrusive illumination of its object space. Another object is to provide such a mirror with provision for defogging.

SUMMARY OF THE INVENTION

The present invention is a dental mirror device, including a handle with an enclosure head on the end. The enclosure has a cover which is partially mirrored and partially transparent, a light source within it, and a concave reflector around the light source to reflect light through the transparent portion of the cover, the reflected light converging in front of the mirror. Heat from the light source keeps the mirror free of fogging.

DRAWING

FIG. 1 is a three dimensional view of a dental mirror of this invention.

FIG. 2 is a sectional elevation of the dental mirror.

FIG. 3 is an enlarged plan view of FIG. 2.

FIGS. 4-7 show other forms of the mirror from FIG. 3.

DESCRIPTION

Referring to FIGS. 1 and 2, the dental mirror of this invention includes a bowl shaped enclosure 10 with a hollow handle 12 extending from it. A glass or clear plastic cover 14 on the enclosure includes a mirror portion 16 and a clear transparent portion 18. The mirror 16 is reflective outward from the device.

A light source or lamp 20 is mounted within the enclosure 10 and connected by wiring 22 through the hollow handle 12 to an energy source, not shown. The light source 20 will be considered as providing a point source of light 21. A concave reflector 24 surrounds the light source 20. The reflector 24 is preferably a spherical or truncated spherical reflector. The point source 21 is slightly forward of the principal focus of the reflector 24, at a distance S1 behind the mirror 16. A peripheral retaining cap 26 is threaded onto the enclosure 10 to hold the cover 14 in place.

The combination of light source 20 and concave reflector 24, with the light source slightly forward of the principal focus of the reflector, produces converging reflected light forward of the cover 14. Direct forward light from the source 20 is blocked by the mirror portion 16 of the cover 14. Light from the source 20 which is reflected by the reflector 24 near its axis is also blocked by the mirror portion 16. Light from the source 20 to the peripheral portion of the reflector 24 is reflected through the transparent portion 18 of the cover and focused at a nominal distance S2 in front of the mirror 16 for intense illumination of objects in front of the mirror.

FIG. 3 shows the presently preferred configuration of the cover 14, its mirror portion 16, and its transparent portion 18. The mirror 16 is round (diameter D1). The transparent portion 18 is an annular ring (diameter D2) around the mirror. The transparent portion 18 thus transmits a ring of light, converging in front of the mirror 16 to illuminate brightly the desired object or surface at a convenient distance in front of the mirror 16.

FIGS. 4 and 5 show other combinations of mirrored and transparent portions of the cover 14. These variations are primarily to provide mirror shapes for specific applications. The cross-shaped mirror in FIG. 4 provides a broader view in orthogonal directions, and may be preferred for viewing bridgework, for example. These and various other forms of the transparent portion 18 will provide slightly different patterns of viewing and illumination as may be desired for certain applications.

The mirror 16 in FIG. 6 is a concave mirror which allows for closer inspection of the objects or surfaces under examination.

In FIG. 2, the reflector 24 is a continuous curved surface behind the light, from one side of the light to the other. But the paraxial reflected light from this reflector is blocked by the mirror 16. In other words, the central portion of the reflector is not effective. Thus, it may be desirable for reasons of economy or simplicity of assembly to provide the reflector 24 in the form of a truncated spherical segment as shown in FIG. 7. The surface of the reflector of FIG. 7 is of the same curvature (e.g. spherical) as that shown in FIG. 2, providing the same focused ring of illumination described above.

I have discovered that light from the source 20 which is reflected from the periphery of the reflector 24 (paraxial reflected rays and direct light from the source both being eliminated by the mirror 14) provides the best object illumination in front of the mirror. As an experiment, I removed the cover 14 (with its mirror 16) from the device to add paraxial reflected light and direct light from the source 20 to the peripheral reflected light. The resulting illumination was unfocused and weakened as compared to the illumination provided by the peripheral reflected light by itself.

In my preferred form of this device, the converging illumination is most intense and effective from about 10 mm in front of the mirror to about 40 mm in front of the mirror, a "depth of focus" of about 30 mm.

In parametric terms the dental mirror device includes an enclosure cover with an outward reflective circular mirror portion of diameter D1 and an annular transparent portion of diameter D2 around the mirror portion: a light source at a distance S1 behind the mirror portion: and a concave reflector behind the light source to reflect and converge light through the transparent annular portion of the cover at a nominal distance S2 in front of the mirror S1 is more than D2/2. D2 is more than $3 \times (D2-D1)$. S2 is approximately $2 \times D1$.

Another feature of this invention is that the light source 20 produces a small amount of heat, enough to keep the mirror 16 from fogging.

The foregoing description of a preferred embodiment of this invention, including any dimensions, angles, or proportions, is intended as illustrative. The concept and scope of the invention are limited only by the following claims and equivalents thereof.

What is claimed is:

1. A dental mirror device, including:
   an enclosure with a handle extending therefrom;
   a cover on said enclosure, said cover including an outward reflective mirror and a transparent portion;
   a light source disposed within said enclosure and adapted for connection through said handle to an energy source; and
   a concave focusing reflector disposed within said enclosure relative to said light source to reflect light from said source through said transparent portion of said cover and to focus said reflected light in front of said mirror.

2. A dental mirror device as defined in claim 1 in which said mirror is circular and said transparent portion is an annular ring around said mirror.

3. A dental mirror device as defined in claim 1 in which said mirror is a concave mirror.

4. A dental mirror device as defined in claim 1 in which said concave reflector is a spherical reflector, and said light source is disposed primarily forward of the principal focus of said spherical reflector.

5. A dental mirror device as defined in claim 1 in which said concave reflector is a truncated spherical segment.

6. A dental mirror device as defined in claim 1 in which said light converges in front of said mirror in a depth of focus of approximately 30 mm.

7. A dental mirror device as defined in claim 1 in which said light converges in front of said mirror in focused illumination from approximately 10 mm in front of said mirror to approximately 40 mm in front of said mirror.

8. A dental mirror device as defined in claim 1, including means to keep said mirror free of fogging.

9. A dental mirror device as defined in claim 8, said light source being effective to keep said mirror free of fogging.

* * * * *